US012649714B2

(12) United States Patent
Biljan et al.

(10) Patent No.: US 12,649,714 B2
(45) Date of Patent: Jun. 9, 2026

(54) PROCESS AND INTERMEDIATES FOR PREPARATION OF OMAVELOXOLONE AND SALTS THEREOF

(71) Applicant: Sicor-Societa Italiana Corticosteroidi s.r.l., Milan (IT)

(72) Inventors: Tomislav Biljan, Krizevci (HR); Ivana Sagud, Gornja Stubica (HR); Dubravka Pavlicic, Zagreb (HR); Maja Matanovic Skugor, Zagreb (HR)

(73) Assignee: Sicor—Societa Italiana Corticosteroidi s.r.l., Milan (IT)

( * ) Notice: Subject to any disclaimer, the term of this patent is extended or adjusted under 35 U.S.C. 154(b) by 334 days.

(21) Appl. No.: 18/371,006

(22) Filed: Sep. 21, 2023

(65) Prior Publication Data

US 2024/0124393 A1 Apr. 18, 2024

(30) Foreign Application Priority Data

Sep. 21, 2022 (EP) .................................... 22197004

(51) Int. Cl.
*C07C 253/30* (2006.01)

(52) U.S. Cl.
CPC .................................. *C07C 253/30* (2013.01)

(58) Field of Classification Search
CPC .................................................... C07C 253/30
See application file for complete search history.

(56) References Cited

U.S. PATENT DOCUMENTS

2004/0002463 A1 * 1/2004 Honda .................... A61P 17/00 558/429

FOREIGN PATENT DOCUMENTS

WO 2004064723 A2 8/2004
WO 2013163344 A1 10/2013
WO 2014176415 A1 10/2014

OTHER PUBLICATIONS

Aube et al. Comprehensive Organic Synthesis II, vol. 6, 2014, pp. 598-635 (Year: 2014).*
De Luca et al. Synlett 2005, 2, 0223-0226 (Year: 2005).*
Verma et al. Tetrahedron 2012, 53, 2373-2376 (Year: 2012).*
Montalbetti et al. Tetrahedron 2005, 61, 10827-10852 (Year: 2005).*
Loudon et al. (J. Org. Chem. 1984, 49, 4272-4276 (Year: 1984).*
Tadashi Honda, et al., "A Novel Dicyanotriterpenoid, 2-Cyano-3, 12-dioxooleana-1,9(11)-dien-28-onitrile, Active at Picomolar Concentrations for Inhibition of Nitric Oxide Production", Bioorganic& Medicinal Chemistry Letters 12 (2002) 1027-1030.
Tadashi Honda, et al., " Synthetic Oleanane and Ursane Triterpenoids with Modified Rings A and C: A Series of Highly Active Inhibitors of Nitric Oxide Production in Mouse Macrophages", J. Med. Chem. 2000, 43, 4233-4246.
Sykes, Peter, "Hofmann, Curtius, Lossen and Schmidt Reactions", A guidebook to mechanism in organic chemistry, 5th ed, Jan. 1, 1981, p. 121.
Extended European Search Report issued in corresponding application EP 23198939.3 dated Mar. 11, 2024 (14 pages).

* cited by examiner

*Primary Examiner* — Matthew P Coughlin
(74) *Attorney, Agent, or Firm* — Carter, DeLuca & Farrell, LLP

(57) ABSTRACT

Disclosed is a process for the preparation of Omaveloxolone and salts thereof, as well as intermediates thereof.

8 Claims, No Drawings

PROCESS AND INTERMEDIATES FOR PREPARATION OF OMAVELOXOLONE AND SALTS THEREOF

FIELD OF THE INVENTION

The present disclosure relates to a process for the preparation of Omaveloxolone and salts thereof. The present disclosure also relates to intermediates for the preparation of Omaveloxolone and salts thereof.

BACKGROUND OF THE INVENTION

Omaveloxolone has the chemical name N-(2-Cyano-3,12-dioxo-28-noroleana-1,9(11)-dien-17-yl)-2,2-difluoropropanamide and the following chemical structure:

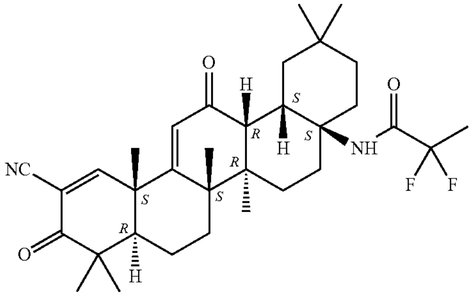

Omaveloxolone is approved under the trade name SKYCLARYS™, formulated in capsules indicated for the treatment of Friedreich's ataxia in adults and adolescents aged 16 years and older. Omaveloxolone is described in publication number WO 2013/163344 as a compound which belongs to nuclear factor erythroid derived 2 (Nrf2) activator. Omaveloxolone is under investigation for a variety of other uses, such as in treating mitochondrial myopathy, advanced solid tumours, metastatic non-small cell lung cancer, melanoma, dermatitis, prevention of corneal endothelial cell loss following cataract surgery, seizures, and protection of healthy cells in radiation treatment. In WO 2013/163344, Omaveloxolone [referred to therein as RTA 408 (63415)] is prepared by the process described in the following Scheme 1.

Scheme 1

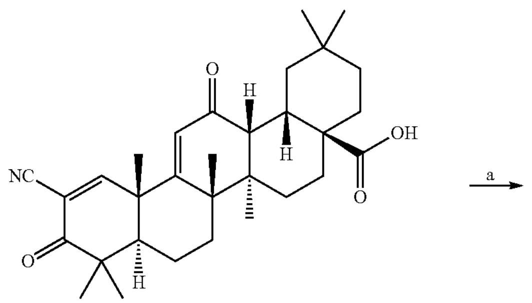

RTA 401

-continued

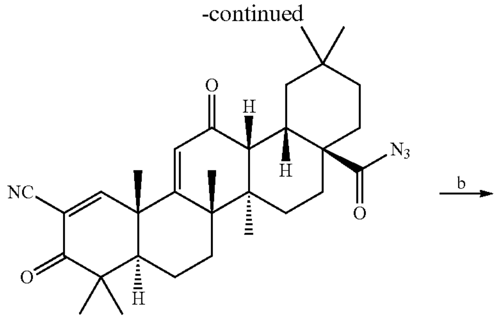

1

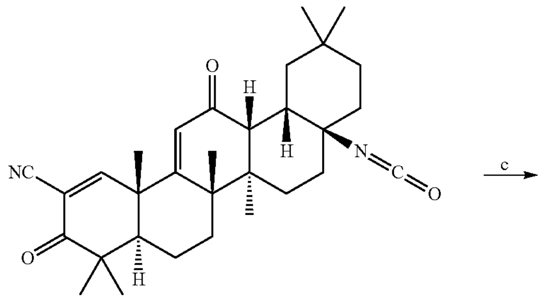

2

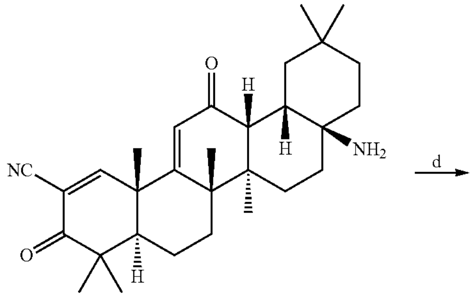

3

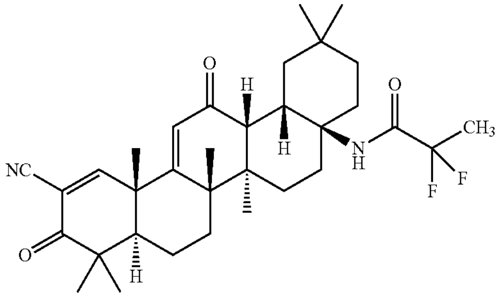

RTA 408 (63415)

According to the above scheme, in step a) the starting material RTA 401 is reacted with Diphenylphosphoryl azide ("DPPA") and forms an azide compound, which is further reacted to prepare Omaveloxolone.

J. Med. Chem. 2000, 43, 4233 describes the preparation of the acid compound RTA 401 from a respective methyl ester compound.

Bioorg. Med. Chem. Lett. 2002, 1027-1030 describes the preparation of dinitrile compounds starting from the acid RTA 401.

The present disclosure provides a simple, safe and efficient process which, unlike the process described in WO 2013/163344, avoids the use of an azide-containing reagent and intermediate. In particular, the process described in WO 2013/163344 requires heating the azide intermediate in order to prepare the intermediate isocyanate. Heating of azides is highly undesirable due the risk of explosion. Moreover, the process disclosed in WO 2013/163344 suffers from a number of disadvantages as well as the undesirable use of azides. In particular, the intermediate compounds 1 and 3, as well as the final compound RTA 408 were obtained only as foams. In the case of intermediate compound 1 and the final compound RT 408, these were obtained as foams despite being subjected to purification by column chromatography. This is particularly problematical and undesirable in large scale synthesis, where solids are desired for ease of processing, handling, storage and purification. Moreover, the use of chromatographic separation procedures in an industrial syntheses is undesirable from an economic perspective due to the large scale use of organic solvents, and energy intensive evaporation process, as well as the need to provide solvent recycling steps.

SUMMARY OF THE INVENTION

In a first aspect, the present disclosure relates to a process for the preparation of Omaveloxolone and salts thereof.

In a second aspect, the present disclosure also relates to use of an intermediate of formula VII, which is described herein below, for the preparation of Omaveloxolone and salts thereof.

The present disclosure further comprises a compound of formula IV-A which is described below, and its use for the preparation of Omaveloxolone and salts thereof.

The process for the preparation of Omaveloxolone of the present disclosure avoids the use of hazardous reagents and intermediate, such as azide-containing compounds, and may produce the final API in a simple, safe and efficient matter. Moreover, in contrast to the process disclosed in WO 2013/163344, where a number of the intermediates, as well as the final compound, are obtained as foams, the use of the starting material of formula VII enables the reaction steps to form Omaveloxolone to proceed via intermediate compounds that are readily isolated as solids, and moreover which may be isolated from the reaction mixtures by simple, less energy-intensive process, such as by precipitation, and without requiring the use of chromatographic purification. Advantageously, the intermediates may be readily isolated as crystalline materials which, if desired, can be purified by recrystallisation.

Omaveloxolone prepared by the process of the present disclosure can be solid. Different solid state forms can be prepared, such as salts, co-crystal and crystalline polymorphs, as well as amorphous form.

The thus prepared Omaveloxolone may be used as a pharmaceutical compound, and or for the preparation of medicament. The medicament can be used in the treatment of Friedreich's ataxia (preferably in adults and adolescents aged 16 years and older), or in the treatment of mitochondrial myopathy, advanced solid tumours, metastatic non-small cell lung cancer, melanoma, dermatitis or seizures; or in the prevention of corneal endothelial cell loss following cataract surgery; or in the protection of healthy cells in radiation treatment.

DETAILED DESCRIPTION OF THE INVENTION

The present disclosure relates to a process for the preparation of Omaveloxolone and salts thereof. The present disclosure also relates to intermediates for the preparation of Omaveloxolone and salts thereof.

The process of the present disclosure avoids the use of hazardous reagents and intermediates, such as azide-containing compounds, and may produce the final API in a simple and efficient matter.

As used herein, the term "isolated" in reference to Omaveloxolone or a solid state form of Omaveloxolone corresponds to Omaveloxolone or a solid state form of Omaveloxolone that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of from about 10 mbar to 50 mbar.

As used herein and unless indicated otherwise, the term "ambient conditions" refer to atmospheric pressure and a temperature of 22-24° C.

As used herein, the term "anhydrous", when referring to reaction conditions preferably means reaction conditions wherein water is present in the reaction in an amount of: about 2% by weight or less, about 1% by weight or less, or about 0.8% by weight or less, about 0.5% by weight or less, about 0.3% by weight or less, about 0.2% by weight or less, about 0.1% by weight or less, about 0.05% by weight or less.

As used herein, the term "anhydrous", when referring to solvents preferably means solvents wherein water is present in the solvent in an amount of: about 2% by weight or less, about 1% by weight or less, or about 0.8% by weight or less, about 0.5% by weight or less, about 0.3% by weight or less, about 0.2% by weight or less, about 0.1% by weight or less, about 0.05% by weight or less.

A compound may be referred to herein as chemically pure or purified compound or as substantially free of any other compounds. As used herein in this context, the expressions "chemically pure", "purified" or "substantially free of any other compounds" will be understood to mean that the pure compound contains: about 20% (w/w) or less, about 10% (w/w) or less, about 5% (w/w) or less, about 2% (w/w) or less, about 1% (w/w) or less, or about 0% of any other compound as measured, for example, by HPLC. Thus, pure or purified Omaveloxolone or Omaveloxolone intermediates described herein as being chemically pure, purified or substantially free of any compounds would be understood to contain greater than about 80% (w/w), greater than about 90% (w/w), greater than about 95% (w/w), greater than about 98% (w/w), greater than about 99% (w/w), or about 100% of the subject Omaveloxolone or Omaveloxolone intermediate. In some embodiments of the disclosure, the described pure, purified Omaveloxolone or Omaveloxolone intermediate may contain from about 1% to about 20% (w/w), from about 5% to about 20% (w/w), or from about 5% to about 10% (w/w) of one or more other compounds. Preferably, the terms "chemically pure", "purified" or "substantially free of any other compounds" with reference to Omaveloxolone or Omaveloxolone intermediates refers to the presence of: about 5% (w/w) or less, about 2% (w/w) or less, about 1% (w/w) or less, about 0.5% (w/w) or less, about 0.2% (w/w) or less, about 0.1% (w/w) or less, or 0.05% (w/w) or less, or about 0% (i.e. undetectable amounts) of any other compound as measured, for example by HPLC.

A compound (Omaveloxolone or an Omaveloxolone intermediate) may also be referred to herein as being enantiomerically pure. By "enantiomerically pure", it is preferably meant that the Omaveloxolone or Omaveloxolone intermediate may contain from: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or 0.05% (w/w) or less, or about 0% (i.e. undetectable amounts), preferably as measured by HPLC, of any other enantiomer of Omaveloxolone, i.e. reference to an enantiomerically pure Omaveloxolone or Omaveloxolone intermediate, preferably means that the Omaveloxolone or Omaveloxolone intermediate contains: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of the desired enantiomer of the Omaveloxolone (i.e. N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide) or the desired enantiomer of the Omaveloxolone intermediate (for example, the Compound VII which is described herein as being enantiomerically pure refers to a compound which contains greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of the enantiomer having the formula:

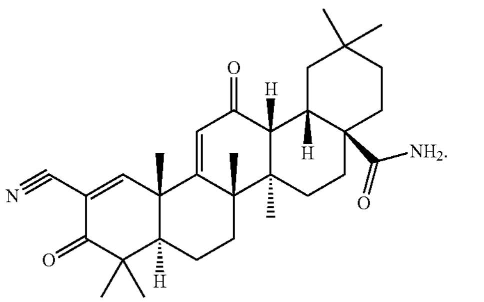

In the present process, the compound of formula VII is advantageously used and converted to Omaveloxolone.

In one aspect the present disclosure provides the use of a compound of formula VII:

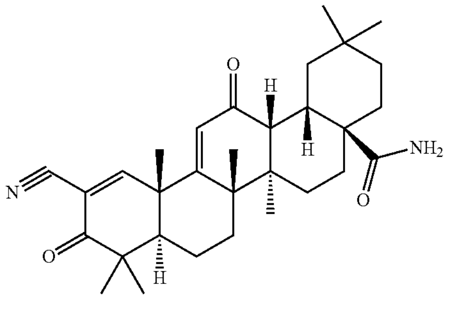

for the preparation of Omaveloxolone. The compound of formula VII may be chemically pure and/or enantiomerically pure. The compound of formula VII may be in solid form, and may be crystalline.

In another aspect the invention provides a process for preparation of Omaveloxolone and salts thereof comprising:

a) reacting the compound of formula VII:

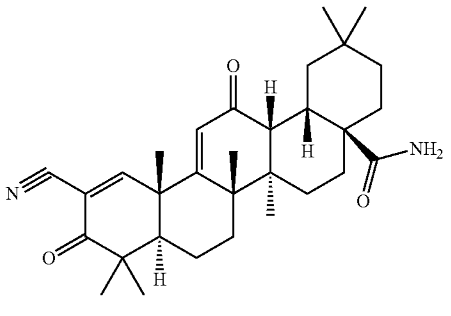

with suitable reagents to obtain a compound of formula IV

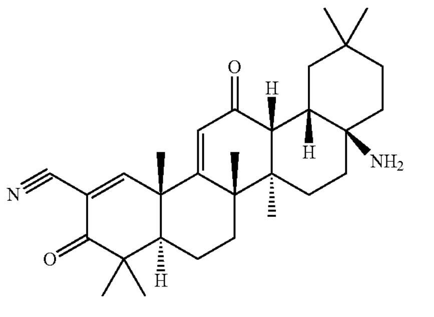

b) converting the compound of formula IV to Omaveloxolone.

The above described process is done under conditions which promote Hofmann rearrangement reaction. Accordingly, the present invention provides a process for the preparation of Omaveloxolone comprising Hofmann rearrangement of a compound of formula VII to form a compound of formula IV [step (a) above], and converting the compound of formula IV to Omaveloxolone [step (b) above]. Thus, step (a) is conducted using suitable Hofmann rearrangement reagent(s) that suitably converts the amide ($CONH_2$) group in Compound VII to the primary amine (—$NH_2$) group in compound IV. According to any aspect or embodiment, the Hofmann rearrangement of step (a) can proceed via the formation of a compound of formula IV-A as described herein, and subsequently an isocyanate intermediate compound of formula III:

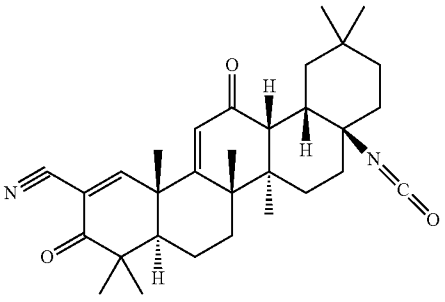

wherein the compound III is subsequently converted to the compound of formula IV. The compound of formula III may be chemically and/or enantiomerically pure. Thus compound III may have a purity of greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100%. The compound of formula III may be enantiomerically pure, preferably containing: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of the compound of formula III. The compound of formula III may be isolated. Preferably, step (a) is carried out without isolation of the compound of formula III as described in any of the embodiments discussed herein.

Particularly, according to any embodiment of the process, step (a) comprises reacting the compound of formula VII with a reagent selected from the group consisting of: bromine, chlorine, hypobromite (particularly sodium hypobromite), hypochlorite (particularly sodium hypochlorite), lead tetraacetate, N-bromosuccinimide, and (bis(trifluoroacetoxy)iodo)benzene (PIFA), and (diacetoxyiodo)benzene (PIDA), preferably PIFA. These reagents can convert the amide group of the compound of formula VII to the compound of formula III as described above, followed by conversion of to the compound of formula IV, for example by the addition of an acid as described in any embodiment herein.

Particularly, the reaction may be carried out using a brominating agent, such as bromine ($Br_2$); or N-Bromosuccinimide (NBS). Alternatively it can be done using sodium hypochlorite (NaOCl), lead tetraacetate (LTA), Diacetoxyiodo)benzene (PIDA) or (Bis(trifluoroacetoxy)iodo)benzene (PIFA).

The reaction in step (a) may be carried out in the presence of a base, preferably wherein the base is selected from the group consisting of: an alkali metal hydroxide, a trialkylamine, preferably a tri($C_1$-$C_4$)alkylamine, and 1,8-diazabicyclo[5.4.0]undec-7-ene (DBU). Preferably, the reaction is done in the presence of sodium hydroxide (NaOH), or triethylamine (TEA).

Particularly, a base may be used with bromine, chlorine, lead tetraacetate, and N-bromosuccinimide reagents. For example, sodium hydroxide may be used with bromine or chlorine, triethylamine may be used with lead tetraacetate, and 1,8-diazabicyclo[5.4.0]undec-7-ene (DBU) may be used with N-bromosuccinimide. Particularly, in any embodiment, when the reagent is selected from (bis(trifluoroacetoxy)iodo)benzene (PIFA) or (diacetoxyiodo)benzene (PIDA), a base is not used.

Particularly, step (a) comprises reacting the compound of formula VII with: bromine or chlorine in the presence of an alkali metal hydroxide (preferably sodium hydroxide); lead tetraacetate (LTA) in the presence of a tri($C_1$-$C_4$)alkylamine base [preferably triethylamine (TEA)]; N-bromosuccinimide in the presence of DBU; (bis(trifluoroacetoxy)iodo)benzene (PIFA); and (diacetoxyiodo)benzene (PIDA). More particularly, in any embodiment, step (a) comprises reacting the compound of formula VII with PIFA. According to any embodiment of the process, step (a) may comprise Hofmann rearrangement reaction of the compound of formula VII with PIFA under acid conditions. Preferably, according to any embodiment of this process, step (a) comprises reacting the compound of formula VII with PIFA or PIDA [preferably PIFA], followed by an acid.

Particularly suitable Hoffman rearrangement reagents for carrying out step (a) are: $Br_2$/NaOH, $Cl_2$/NaOH, sodium hypochlorite, sodium hypobromite, lead tetraacetate/triethylamine, and N-bromosuccinimide (NBS)/1,8-Diazabicyclo[5.4.0]undec-7-ene (DBU), phenyl iodosyl bis(trifluoroacetate) (PIFA), and iodosobenzene diacetate (PIDA). More particularly, $Br_2$/NaOH, $Cl_2$/NaOH, sodium hypochlorite, or sodium hypobromite may be used. In especially preferred embodiments, step (a) comprises reacting the compound of formula VII with PIFA followed by an acid.

The present disclosure provides a process for preparation of Omaveloxolone and salts thereof comprising: (a) Hofmann rearrangement of the compound of formula VII as described above to form a compound of formula IV as described above, and (b) converting the compound of formula IV to Omaveloxolone, wherein step (a) is carried out by a process comprising reacting the compound of formula VII with (bis(trifluoroacetoxy)iodo)benzene (PIFA). Preferably, the present disclosure provides a process for preparation of Omaveloxolone and salts thereof comprising: (a) Hofmann rearrangement of the compound of formula VII to form a compound of formula IV, and (b) converting the compound of formula IV to Omaveloxolone, wherein step (a) is carried out by a process comprising reacting the compound of formula VII with PIFA under acidic conditions, particularly wherein step (a) comprises reacting the compound of formula VII with PIFA followed by reaction with an acid.

According to any aspect or embodiment of the processes as described herein, step (a) is preferably conducted in a solvent, which may be from the group consisting of: ethers (particularly $C_4$-$C_8$ ethers, more particularly $C_2$-$C_6$ ethers, and especially diethyl ether, tetrahydrofuran, diisopropyl ether), ketones (particularly $C_3$ to $C_8$ ketones, more particularly $C_3$-$C_6$ ketones, especially acetone, cyclohexanone, methylisobutyl ketone), nitriles (particularly $C_2$-$C_8$ nitriles, more particularly $C_2$-$C_4$ nitriles, especially acetonitrile), water, and combinations thereof, preferably wherein the reaction in step (a) is carried out in a solvent comprising water, and optionally with a ether, ketone, ester or nitrile which is miscible with water.

The reaction in step (a) may be conducted at a temperature of: about 40° C. to about 180° C., about 50° C. to about 160° C., about 60° C. to about 150° C., about 70° C. to about 140° C., about 80° C. to about 120° C., or about 80° C. to about 100° C.

Alternatively, according to any aspect or embodiment of the processes as described herein wherein the Hofmann rearrangement reagent is either phenyl iodosyl bis(trifluoroacetate) (PIFA), and iodosobenzene diacetate (PIDA), the reaction may be carried out in a polar aprotic solvent, preferably selected from the group consisting of tetrahydrofuran (THF), 2-methyltetrahydrofuran (Me-THF), N,N-dimethylformamide (DMF), and DMSO, more preferably THF or Me-THF, and most preferably THF. Preferably, the polar aprotic solvent is anhydrous. In any embodiment of this process, the reaction with the Hofmann rearrangement reagent may be carried out in anhydrous conditions.

Alternatively, when the Hofmann rearrangement reaction in step (a) is carried out using PIFA or PIDA (preferably PIFA), the reaction temperature preferably should not exceed about 30° C., or should not exceed about 25° C. Preferably, according to any embodiment wherein PIFA or PIDA is used, the reaction is carried out at a temperature of: about 5° C. to about 30° C., about 10° C. to about 25° C., about 15° C. to about 22° C., about 18° C. to about 22° C., or at about room temperature. This reaction may form an isocyanate intermediate of formula III which may be readily converted to the compound IV under acidic conditions. Accordingly, following the reaction with the Hofmann rearrangement reagent, particularly PIFA or PIDA, an acid is preferably added. Preferably, the reaction mixture is cooled, preferably to about −10° C. to about 10° C., about −5° C. to about 8° C., or about 0° C. to about 5° C., prior to the addition of acid. The acid is preferably a mineral acid, more preferably hydrochloric acid, sulfuric acid, nitric acid, or phosphoric acid, most preferably hydrochloric acid, and especially concentrated hydrochloric acid. The acid is preferably added portionwise, or dropwise. It is preferred that during the addition of the acid, the reaction mixture should not exceed about 30° C., or should not exceed about 25° C. The reaction mixture may be maintained temperature of: about 0° C. to about 20° C., about 5° C. to about 15° C., or about 10° C., during the addition of the acid. Preferably, prior to the addition of the acid, the reaction mixture is cooled to a temperature of about −5° C. to about 20° C., about 0° C. to about 15° C., or about 0° C. to about 5° C. After the addition of acid, the reaction mixture may be stirred, preferably at a temperature of: about 0° C. to about 20° C., about 5° C. to about 15° C., about 10° C. to about 12° C., or about 10° C. The reaction mixture may be maintained at this temperature for: about 4 hours to about 48 hours, about 6 hours to about 36 hours, about 6 hours to about 24 hours, about 6 hours to about 12 hours, or about 6 hours to about 8 hours. Advantageously, the compound of formula IV can be readily isolated from the reaction mixture by basifying and extraction. Preferably, according to any embodiment, the base may be an organic base, particularly selected from the group consisting of pyridine, pyrrolidine, N-methylpyridine, N-methyl-piperidine, morpholine, and N-methylmorpholine (NMM)). The extraction solvents may comprise water and/or an organic solvent selected from the group consisting of: diethyl ether, diisopropyl ether, ethylacetate, and methylisobutyl ketone; preferably a mixture of water and an organic solvent selected from: diethyl ether, diisopropyl ether, ethylacetate, and methylisobutyl ketone; and more preferably a mixture of water and ethylacetate. After extracting into the organic solvent, the compound of formula IV may be isolated as a solid, preferably as a crystalline solid, by evaporation, and/or by the addition of antisolvent, preferably wherein the anti-solvent is selected from a $C_6$-$C_{10}$ alkane, preferably n-heptane.

According to any aspect or embodiment, the compound of formula IV may be converted to Omaveloxolone by reaction with 2,2-difluoropropanoic acid. Accordingly, in any aspect or embodiment of the above-described process, step (b) comprises reacting the compound of formula IV with 2,2-difluoropropanoic acid to form Omaveloxolone. In any aspect or embodiment, step (b) may be carried out in the presence of a coupling agent and optionally a base. Particularly, the coupling agent may be dicyclohexylcarbodiimide (DCC) or 2-chloro-4,6-dimethoxy-1,3,5-triazine (CDMT), preferably CDMT. In any aspect or embodiment, step (b) is carried out in the presence of a base. Particularly, the base may be selected from an organic base, and more particularly 4-(dimethylamino)pyridine (DMAP) or N-methylmorpholine (NMM), more particularly NMM. In any aspect or embodiment, the compound of formula IV may be converted to Omaveloxolone by reaction with 2,2-difluoropropanoic acid in the presence of CDMT and NMM. According to any embodiment, step (b) may be conducted in a solvent, preferably the solvent is an aprotic solvent, particularly selected from the group consisting of tetrahydrofuran (THF), 2-methyltetrahydrofuran (2-MeTHF), DMF or DMSO, more particularly THF or 2-MeTHF, acetonitrile (ACN), ethylacetate, and most particularly 2-Me-THF. According to any embodiment, step (b) may comprise combining the compound of formula IV with the coupling agent, base, and solvent; preferably step (b) comprises combining the compound of formula IV with a mixture comprising CDMT and NMM in the solvent (preferably 2-MeTHF) and adding the compound IV to the mixture. The compound of formula IV may be added as a solution, preferably in the same reaction solvent. The addition of compound IV may be carried out at a temperature of from: about −10° C. to about 15° C., about −5° C. to about 10° C., or about 0 to about 5° C. The Omaveloxolone may be readily isolated from the reaction solution by filtration (to remove any solids), washing the organic solution, and precipitation and/or evaporation. The Omaveloxolone can be easily purified by recrystallization using any suitable solvent or solvent/antisolvent combination. In any embodiment, the Omaveloxolone may be recrystallised from a solvent/antisolvent combination, wherein the solvent is preferably tetrahydrofuran (THF) or 2-methyltetrahydrofuran (2-MeTHF), and the antisolvent is hexane or heptane, preferably wherein the antisolvent is heptane (particularly n-heptane).

The present disclosure further comprises Omaveloxolone obtainable by a process according to any embodiment described herein. The Omaveloxolone which is obtainable by the process according to any embodiment described herein may advantageously be chemically pure, preferably which has a purity of: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100%. The Omaveloxolone which is obtainable by the process according to any embodiment described herein may advantageously be enantiomerically pure, preferably containing: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide.

The present disclosure further comprises a compound of formula IV-A:

IV-A

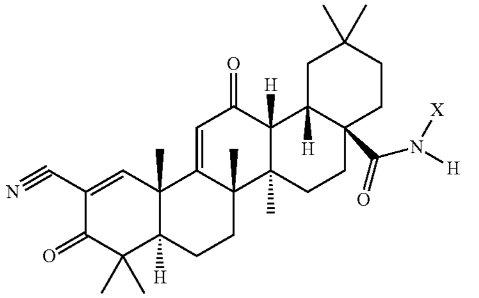

where X is selected from the group consisting of halogen, such as chloro, bromo or iodo; or $Pb(OAc)_3$. Alternatively, X in the compound of formula IV-A may be selected from the group consisting of:

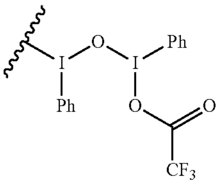

or

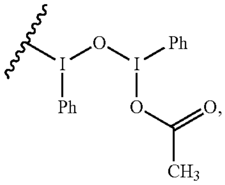 [SMILES: *I(OI(OC(=O)C(F)(F)F)c1ccccc1)c1ccccc1]

and preferably wherein X is:

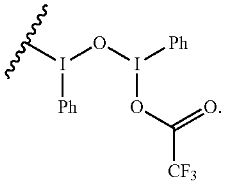

The compound of formula IV-A may be formed as an intermediate in the Hofmann rearrangement reaction and may be isolated, but preferably the compound of formula IV-A is converted to the compound of formula III in situ. The compound of formula IV-A may be chemically and/or enantiomerically pure. Thus compound IV-A may have a purity of greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100%.

The compound of formula IV-A may be enantiomerically pure, preferably containing: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of the compound of formula IV-A.

The compound IV-A may be in solution, or may be in solid form, and may be crystalline. Preferably the compound IV-A may be in solution.

The present disclosure also comprises the compound of formula IV-A for use in the preparation of Omaveloxolone. Typically the compound of formula IV-A may be converted in situ to the isocyanate intermediate of formula III as described above, and the compound of formula III is converted to the corresponding amine of formula IV. The amine of formula IV is reacted with 2,2-difluoropropanoic acid to form Omaveloxolone. In specific embodiments, the present disclosure comprises a process for preparation of Omaveloxolone comprising preparation of compound of formula IV-A, for example by the process of the present disclosure, and converting it to Omaveloxolone.

The present disclosure further provides chemically and/or enantiomerically pure Omaveloxolone.

The present disclosure further includes the use of a compound of formula VII or IV-A:

IV-A

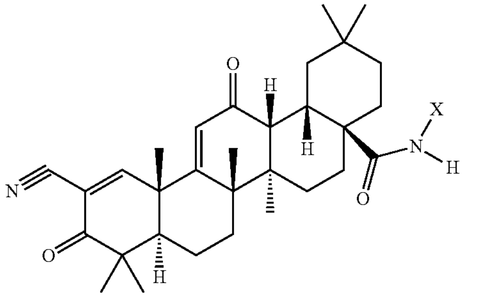

where X is selected from the group consisting of chloro, bromo, iodo, or $Pb(OAc)_3$, particularly chloro, bromo, or iodo, and more particularly bromo; or wherein X is selected from the group consisting of:

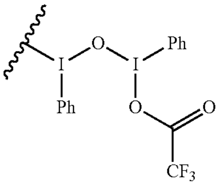

or

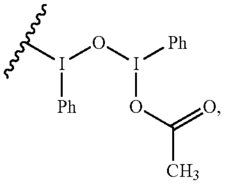 [SMILES: *I(OI(OC(=O)C(F)(F)F)c1ccccc1)c1ccccc1]

and preferably wherein X is:

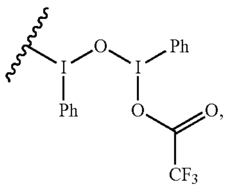

for the preparation of a compound of formula IV, or Omaveloxolone or a salt thereof.

Also disclosed is a process for the preparation of a compound of formula (IV):

IV

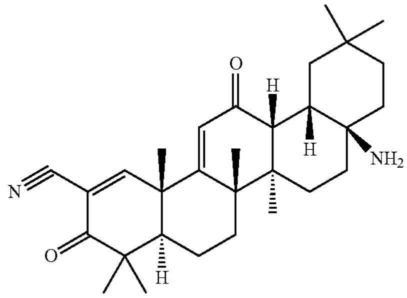

comprising Hofmann rearrangement of a compound of Formula VII:

VII

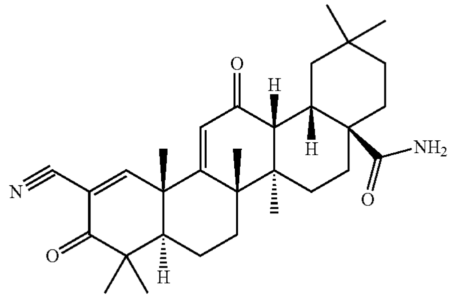

The compound of formula VII may be prepared by a process comprising:

(i) reacting the carboxylic acid group in the compound of formula OMV-1:

OMV-1

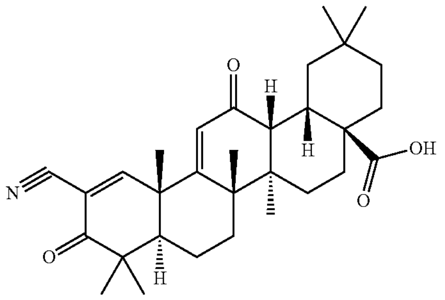

to form a compound of formula OMV-12A:

OMV-12A

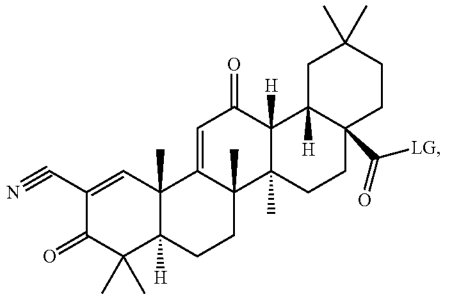

wherein LG is a leaving group, preferably fluoro, chloro or bromo, and more preferably chloro; and (ii) aminolysis of the compound of formula OMV-12A to form the compound VII:

VII

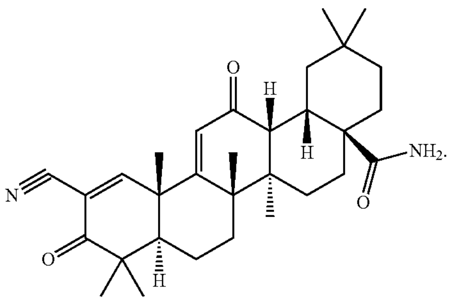

Preferably, the group LG in formula OMV-12A is chloro, i.e. compound OMV-12:

OMV-12

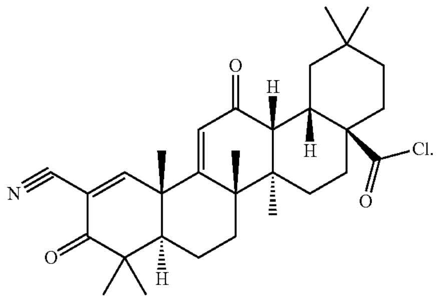

In any embodiment of this process, step (i) may be carried out in the presence of one or more solvents, preferably one or more aprotic solvents. Preferably the solvent may comprise a hydrocarbon (particularly a $C_5$ to $C_{10}$ hydrocarbon, and more particularly toluene), and/or a polar aprotic solvent, preferably tetrahydrofuran (THF), 2-methyltetrahydrofuran (2-MeTHF), dimethylsulfoxide (DMSO) or N,N-dimethylformamide (DMF), more preferably DMF. In any embodiment of this process, the group LG in compound OMV-12A is chloro, and step (i) comprises reacting the compound of formula OMV-1 with thionyl chloride or phosphorus oxychloride, oxalyl chloride, preferably thionyl chloride. According to any embodiment of this process, the reagent in step (i) may be added to a cooled solution of OMV-1 in the solvent(s), particularly wherein the solution is cooled to a temperature of: about −10° C. to about 10° C., about −5° C. to about 8° C., or about 0° C. to about 5° C., preferably about −0° C. to about 5° C. After the addition, the reaction mixture may be stirred, particularly at about room temperature. According to any embodiment of this process, step (i) is carried out in a solvent comprising toluene and DMF. According to any embodiment of this process, the compound of formula OMV-12A obtained in step (i) may be isolated, for example by precipitation directly from the reaction mixture, and can be used in step (ii) without further purification. Advantageously, the compound of formula OMV-12A may be obtained as a crystalline product having high purity directly from the reaction mixture, preferably without reaction work-up steps, and more preferably by precipitation directly from the reaction mixture, for example by the addition of an antisolvent, such as an alkane (particularly a $C_5$ to $C_8$ alkane, and more particularly n-heptane), and can be used in step (ii) without further purification. According to any embodiment of this process, step (ii) may be carried out in a suitable solvent, preferably a polar aprotic solvent, more preferably tetrahydrofuran. According to any embodiment, step (ii) may be carried out by combining the compound of formula OMV-12A, preferably as a solution in the solvent, with ammonia or ammonium hydroxide. The ammonia or ammonium hydroxide may be provided as a solution in a solvent, preferably the same solvent as for compound OMV-12A. More preferably, step (ii) comprises addition of a solution of the compound of formula OMV-12A to a solution of ammonia or ammonium hydroxide. The addition of the solution of the compound of formula OMV-12A may be carried out dropwise. Advantageously, the product compound VII from step (ii) of this process may be readily isolated as a crystalline material having high purity directly from the reaction mixture, preferably without work-up steps, and more preferably by direct filtration of the reaction mixture.

Alternatively, compound (VII) may be prepared by a process comprising:

(i) reacting the compound of formula OMV-1:

OMV-1

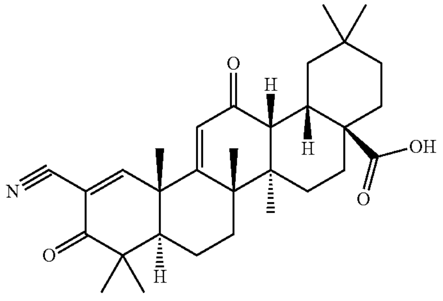

with 1,1'-carbonyldiimidazole (CDI) to form a compound of formula OMV-13:

OMV-13

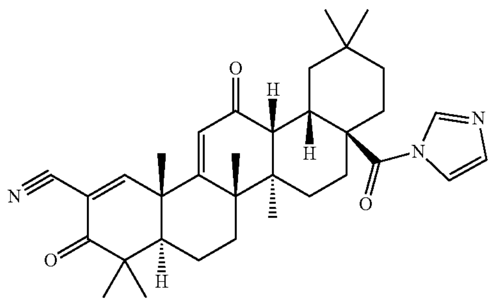

(ii) reacting the compound of formula OMV-13 with ammonia or ammonium hydroxide to form the compound VII:

VII

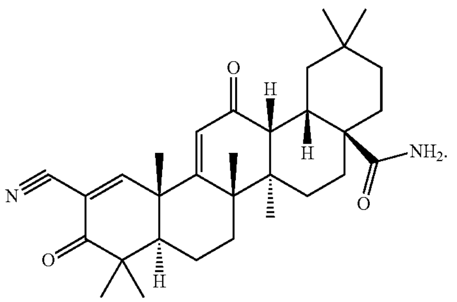

In any embodiment of this process, step (i) may be carried out in the presence of one or more solvents, preferably one or more aprotic solvents. Preferably the solvent comprises a polar aprotic solvent, preferably THF, 2-MeTHF, DMSO or DMF, and more preferably the solvent comprises THF. According to any embodiment of this process, step (i) may be carried out at a temperature of: about 20° C. to about 80° C., about 30° C. to about 70° C., or about 40° C. to about 60° C., preferably about 45° C. to about 55° C., or about 50° C. According to any embodiment, step (ii) may be carried out without isolating the compound of formula OMV-13. Preferably, according to any embodiment. in step (ii) compound OMV-13 is reacted with ammonia or ammonium hydroxide in situ, i.e. steps (i) and (ii) may be carried out in one pot. In any embodiment of the process, step (ii) may comprise reaction of OMV-13 with ammonia, preferably in a solvent comprising a polar aprotic solvent, preferably THF, 2-MeTHF, DMSO or DMF, and more preferably THF. In any embodiment of the process, step (ii) may comprise addition of ammonia gas to a solution of compound OMV-13 in THF, preferably wherein the solution of OMV-13 in THF is obtained directly as the reaction mixture from step (i). In any embodiment of the process, the reaction with ammonia gas in step (ii) may be carried out under pressure. Step (ii) may further comprise removal of the reaction solvent, for example by evaporation, and addition of an acid, preferably acetic acid, and optionally a polar aprotic solvent, particularly THF, 2-MeTHF, DMF or acetonitrile, more preferably acetonitrile. The reaction in step (ii) may be carried out at a temperature of: about 50° C. to about 125° C., about 60° C. to about 115° C., or about 70° C. to about 105° C., preferably about 80° C. to about 100° C., or about 90° C. to about 95° C. The compound of formula (VII) may be isolated from the mixture by crystallisation. The crystallisation may comprise precipitation by the addition of an antisolvent. Preferably, the antisolvent is water. Preferably the antisolvent is added dropwise. Optionally seed crystals of compound (VII) [for example, as prepared by the preceding process as described above] may be added to facilitate crystallisation. Advantageously, the compound of formula (VII) may be obtained as a crystalline material in high purity from the reaction mixture.

According to any aspect or embodiment of the processes for preparing the compound VII as described herein, the starting material of formula OMV-1 may be prepared by hydrolysis of the ester group of compound VI (Bardoxolone methyl):

VI

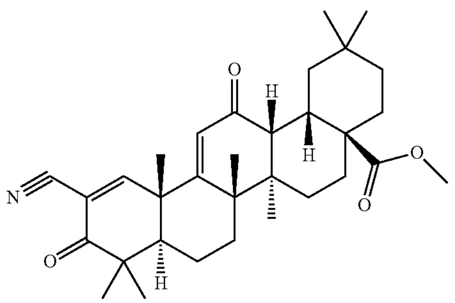

to form the corresponding acid OMV-1 (Bardoxolone). The reaction may be carried out using lithium iodide, and a base, preferably an organic base, more preferably pyridine. The reaction may be carried out in a polar aprotic solvent, preferably DMF, THF, 2-MeTHF or DMSO, and more preferably DMF. In any embodiment of the process, a solution of the compound VI in the solvent may be added to the mixture containing the organic base and lithium iodide. Preferably, a solution of the compound VI in DMF is added to a mixture of pyridine and lithium iodide in DMF. The addition of the solution of the compound VI in DMF may be carried out dropwise. Following the reaction, the mixture may be acidified, preferably with a mineral acid, more preferably hydrochloric acid. Prior to the acidification, water may be added. Advantageously, after acidification, the product may be crystallised directly from the reaction mixture, for example by heating and cooling. The product OMV-1 may be isolated by filtration, and optionally recrystallised. Particularly suitable recrystallization solvents are dichloromethane and n-heptane. The compound of formula OMV-1 can be obtained as a crystalline material in quantitative or near quantitative yields and in high purity in this process.

According to any aspect or embodiment of processes described herein, the process may further comprise combining the Omaveloxolone with at least one pharmaceutically acceptable salt to form a pharmaceutical composition.

Having described the disclosure with reference to certain preferred embodiments, other embodiments will become apparent to one skilled in the art from consideration of the specification. It will be apparent to those skilled in the art that many modifications, both to materials and methods described, may be practiced without departing from the scope of the claims.

The following non-limiting examples illustrate methods according to the disclosure.

Example 1

Preparation of 2-Cyano-3,12-dioxooleana-1,9(11)-dien-28-oic Acid (OMV-1)

Into a 1 litre reactor, DMF (180 ml; 3 V), pyridine (86 ml; 1.07 mol; 9.0 eq.) and LiI (206.5 g; 1.54 mol; 13.0 eq.) were added under inert atmosphere and heated to 122-128° C. 2-Cyano-3,12-dioxooleana-1,9(11)-dien-28-oic acid methyl ester (Bardoxolone methyl, Compound VI) (60.0 g; 0.19 mol; was dissolved in DMF (300 ml; 5 V) and added dropwise to the reaction mixture. After reaction completion the reaction mixture was cooled down to 45-50° C. and water (1620 ml; 27 V) was added dropwise. Concentrated HCl (37% (aq), 99 ml; 10 eq.) was added dropwise. The suspension was heated to 65-70° C. and stirred for 3 hours, cooled to RT and stirred for 1 h. Crystals were filtered off, washed with water and dried at 60° C. under vacuum to give crude crystals of Bardoxolone, which were recrystallized from DCM/n-heptane (1:2) by dissolving in dichloromethane (3V), heating to 35° C. to 40° C., and adding n-heptane (6V), followed by cooling, to give OMV-1 (Bardoxolone).

Example 2

Preparation of 2-Cyano-3,12-dioxooleana-1,9(11)-dien-28-amide (Compound VII)

Into round bottom flask, OMV-1 (Bardoxolone) (8.0 g; 0.016 mol), toluene (40 ml; 5 V) and N,N-dimethylformamide (DMF) (0.16 ml; 0.02 mol) were added and cooled down to 0-5° C. Thionyl chloride (1.89 ml; 0.026 mol; 1.6 eq.) was added dropwise. The reaction mixture was stirred at RT until reaction completion, after which n-heptane (40 ml; 5 V) was added. The suspension was cooled down to 0-5° C. and stirred for 1 h. Crystals of the acyl chloride (OMV-12) were filtered off, washed with n-heptane and dissolved in THF (96 ml; 12 V). The solution was added dropwise to a mixture of THF (96 ml; 12 V) and 25% $NH_4OH$ (9.8 ml; 0.13 mol; 8.0 eq) at 0-5° C. The suspension was stirred overnight at 0-5° C. The resulting crystals were filtered off, washed with THF and dried at 50° C. under vacuum, and recrystallised in acetic acid/water (1:2) by dissolving in acetic acid under heating at 70° C. to 75° C., and adding water. The product was isolated by filtration and dried at 50° C. under vacuum.

Example 3

Preparation of 2-Cyano-3,12-dioxooleana-1,9(11)-dien-28-amide (Compound VII)

Into 1 litre reactor Bardoxolone (30.0 g; 0.060 mol), THF (300 ml; 10 V) and 1,1'-carbonyldiimidazole (CDI) (19.8 g; 0.122 mol; 2.0 eq.) were charged. The reaction mixture was warmed to 50° C. and stirred until reaction completion. $NH_3$ (g) 1 bar pressure was applied and the reaction mixture stirred overnight. THF was evaporated. Acetic acid (300 ml; 10 V) and acetonitrile (60 ml; 2 V) were added. The mixture was heated to 90-95° C. and water (360 ml; 12 V) was added dropwise. The solution was cooled down to 70-75° C. and seeded with Compound VII (e.g. as prepared from Example 2). The suspension was cooled down to 60-65° C. and stirred for 2.5 h, cooled down to 20-25° C. and stirred overnight and then cooled down to 0-5° C. and stirred for additional 2 h. Crystals were filtered off, washed with water and dried at 50° C. under vacuum.

Example 4

Preparation of 17-Amino-3,12-dioxo-28-noroleana-1,9(11)-diene-2-carbonitrile (Compound IV)

2-Cyano-3,12-dioxooleana-1,9(11)-dien-28-amide (compound VII) (17.0 g; 0.034 mol) and (bis(trifluoroacetoxy)iodo)benzene (PIFA) (15.9 g; 0.037 mol; 1.1 eq.) were dissolved in dry THF (170 ml; 10 V) and stirred for 1 hour at RT. The solution was cooled down to 0-5° C. and 37% HCl (28 mL, 0.340 mol; 10.0 eq.) was added dropwise. The reaction mixture was stirred overnight at 10-12° C. Complete conversion was observed. Water (85 ml; 5 V) and ethylacetate (EtOAc) (170 mL; 10 V) were added and N-methylmorpholine (NMM) (44 mL, 0.405 mol; 12 eq.) was added dropwise while maintaining the temperature at 0-5° C., followed by addition of water (61 mL; 5 V) and extraction. The layers were separated and the organic layer was washed once with water (170 mL; 10 V). The EtOAc was concentrated to 5 V and compound IV was precipitated by dropwise addition of n-heptane (170 ml; 10 V) at RT. The suspension was stirred at RT overnight, and additionally at 0-5° C. for 5 h. The product was filtered off, washed with EtOAc:n-heptane 1:2 mixture and dried at 50° C. under vacuum to give compound IV.

Example 5

Preparation of N-(2-Cyano-3,12-dioxo-28-noroleana-1,9(11)-dien-17-yl)-2,2-difluoropropanamide) (Omaveloxolone, OMV)

2-chloro-4,6-dimethoxy-1,3,5-triazine (CDMT) (3.98 g, 0.023 mol; 3.0 eq.) was dissolved in 2-MeTHF (35 ml; 10 V) and NMM (4.16 mL, 0.038 mol; 5.0 eq.) was added dropwise at 0-5° C. The mixture was stirred for 10 min. 17-Amino-3,12-dioxo-28-noroleana-1,9(11)-diene-2-carbonitrile (3.5 g, 0.0076 mol) was dissolved in 2-MeTHF (35 ml; 10 V) and added to reaction mixture followed by addition of 2,2-difluoropropanoic acid (1.66 g, 0.015 mol; 2.0 eq.) dissolved in 2-MeTHF (3.5 ml; 1 V). The reaction mixture was stirred until complete conversion (1 h). The solid by-products were filtered off from reaction mixture. The filtrate was washed with half-saturated solution of $NH_4Cl$ (70 ml; 20 V), 5% solution of $NaHCO_3$ (70 ml; 20 V) and 5% solution of NaCl (70 ml; 20 V). The organic layer was collected and evaporated to dryness and the residue was crystallized from MeTHF/n-heptane (1:1) by dissolution in 2-MeTHF and addition of n-heptane to obtain white crystals of Omaveloxolone.

Example 6

Preparation of N-(2-Cyano-3,12-dioxo-28-noroleana-1,9(11)-dien-17-yl)-2,2-difluoropropanamide) (Omaveloxolone, OMV)

2-Cyano-3,12-dioxooleana-1,9(11)-dien-28-amide (compound VII) (0.5 g; 0.00102 mol) and PIFA (0.53 g; 0.0122 mol; 1.2 eq.) were dissolved in THF (5 ml; 10 V) and stirred for 1 hour at RT. The solution was cooled down to 0-5° C. and 37% HCl (0.42 mL, 0.0051 mol; 5.0 eq.) was added dropwise. The reaction mixture was stirred overnight at 5-10° C. Complete conversion was observed. Product compound IV precipitated as HCl salt from reaction mixture. NMM was added to the reaction mixture (0.67 mL, 0.0061 mol; 6.0 eq.) and stirred for 30 min. The aqueous layer was separated and the THF layer was used to next step without isolation of product. CDMT (0.54 g, 0.0031 mol; 3 eq.) was suspended in THF (4 ml) and NMM (0.53 ml, 0.0051 mol; 5 eq.) was added dropwise and stirred for 15 min. The THF solution of compound IV from the previous step was added dropwise, followed by the addition of 2,2-difluoropropanoic acid (0.22 g, 0.0020 mol; 2.0 eq.) dissolved in THF (0.5 ml). The reaction mixture was stirred for 1 h until complete conversion. The solid was filtered off, and the reaction mixture was evaporated to dryness. The residue was dissolved in isopropanol (3 ml) by heating to reflux, and n-heptane (3 mL) was added dropwise. The solution was cooled down to RT and stirred for 1 hour. The obtained suspension was stirred at RT for 1 h. Crystals of Omaveloxolone were filtered off, washed with isopropanol:n-heptane 1:1 and dried at 50° C., vacuum. White crystals of N-(2-Cyano-3,12-dioxo-28-noroleana-1,9(11)-dien-17-yl)-2,2-difluoropropanamide were obtained.

Further aspects and embodiments of the disclosure are set out in the numbered clauses below:

1. A process for preparation of Omaveloxolone or a salts thereof, comprising:
   (a) Hofmann rearrangement reaction of a compound of Formula VII:

VII

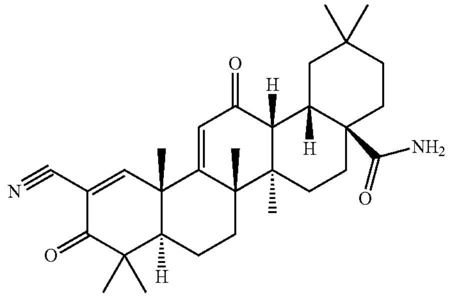

to form a compound of formula IV:

IV

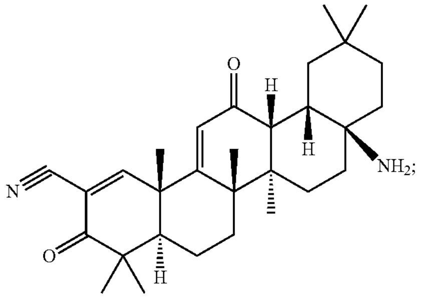

and (b) converting the compound of formula IV to Omaveloxolone.
2. A process according to Clause 1, wherein step (a) comprises reacting the compound of formula IV with a reagent selected from the group consisting of: bromine, chlorine, sodium hypobromite, sodium hypochlorite, lead tetraacetate, N-bromosuccinimide, and (bis(trifluoroacetoxy)iodo)benzene (PIFA), and (diacetoxyiodo)benzene (PIDA).

3. A process according to Clause 1 or Clause 2, wherein the reaction in step (a) is carried out in the presence of a base, preferably wherein the base is selected from the group consisting of: an alkali metal hydroxide, a trialkylamine preferably a tri($C_1$-$C_4$)alkylamine, and 1,8-diazabicyclo[5.4.0]undec-7-ene (DBU).
4. A process according to any of Clauses 1, 2 or 3, wherein step (a) is carried out with a reagent selected from the group consisting of:
   bromine or chlorine in the presence of an alkali metal hydroxide, preferably wherein the alkali metal hydroxide is sodium hydroxide;
   sodium hypochlorite;
   sodium hypobromite;
   lead tetraacetate in the presence of a trialkylamine, preferably a tri($C_1$-$C_4$)alkylamine, and more preferably triethylamine;
   N-bromosuccinimide in the presence of 1,8-diazabicyclo[5.4.0]undec-7-ene;
   (bis(trifluoroacetoxy)iodo)benzene (PIFA); or
   (diacetoxyiodo)benzene (PIDA).
5. A process according to any of Clauses 1, 2, 3, or 4, wherein the reaction in step (a) is carried out with PIFA or PIDA.
6. A process according to any of Clauses 2, 3, 4, or 5, wherein the reagent in step (a) is PIFA.
7. A process according to any of Clauses 2, 3, 4, 5, or 6, wherein the reaction is carried out in a solvent, preferably wherein the solvent is selected from the group consisting of: ethers (particularly $C_4$-$C_8$ ethers, more particularly $C_2$-$C_6$ ethers, ketones (particularly $C_3$ to $C_8$ ketones, more particularly $C_3$-$C_6$ ketones, nitriles, water, and combinations thereof; or wherein the solvent is a polar aprotic solvent, preferably selected from the group consisting of N,N-dimethylformamide (DMF) and dimethylsulfoxide (DMSO); preferably wherein the solvent is selected from the group consisting of: diethyl ether, tetrahydrofuran, 2-methyltetrahydrofuran, diisopropyl ether, acetone, ethylacetate, cyclohexanone, methylisobutyl ketone, acetonitrile, DMF, and DMSO, or a mixture thereof.
8. A process according to Clause 7, wherein the solvent is selected from the group consisting of: diethyl ether, tetrahydrofuran, 2-methyltetrahydrofuran, or diisopropyl ether.
9. A process according to Clause 8 wherein the solvent is tetrahydrofuran.
10. A process according to any of Clauses 1, 2, 3, 4, 5, 6, 7, 8, or 9, wherein step (a) comprises reacting the compound of formula VII with PIFA, in a solvent which is tetrahydrofuran.
11. A process according to any of Clauses 1, 2, 3, 4, 5, 6, 7, 8, 9, or 10, wherein the solvent is selected from the group consisting of: ethers (particularly $C_4$-$C_8$ ethers, more particularly $C_2$-$C_6$ ethers), ketones (particularly $C_3$ to $C_8$ ketones, more particularly $C_3$-$C_6$ ketones), nitriles, and combinations thereof or wherein the solvent is a polar aprotic solvent, preferably selected from the group consisting of N,N-dimethylformamide (DMF) and dimethylsulfoxide (DMSO); and most preferably wherein the solvent is THF; wherein the solvent is anhydrous, preferably wherein water is present in the solvent in an amount of: about 2% by weight or less, about 1% by weight or less, or about 0.8% by weight or less, about 0.5% by weight or less, about 0.3% by weight or less, about 0.2% by weight or less, about 0.1% by weight or less, about 0.05% by weight or less.
12. A process according to any of Clauses 1, 2, 3, 4, 5, 6, 7, 8, 9, 10, or 11, wherein the reaction is carried out in anhydrous conditions, preferably wherein water is present in the reaction in an amount of: about 2% by weight or less, about 1% by weight or less, or about 0.8% by weight or less, about 0.5% by weight or less, about 0.3% by weight or less, about 0.2% by weight or less, about 0.1% by weight or less, about 0.05% by weight or less.
13. A process according to any of Clauses 1, 2, 3, 4, 5, 6, 7, 8, 9, 10, 11, or 12, wherein the reaction is carried out at a temperature of: about 5° C. to about 30° C., about 10° C. to about 25° C., about 15° C. to about 22° C., about 18° C. to about 22° C., or at about room temperature.
14. A process according to any of Clauses 2, 3, 4, 5, 6, 7, 8, 9, 10, 11, 12, or 13, wherein after reaction, an acid is added, preferably wherein the acid is a mineral acid, more preferably hydrochloric acid, sulfuric acid, nitric acid, or phosphoric acid.
15. A process according to any of Clauses 1, 2, 3, 4, 5, 6, 7, 8, 9, 10, 11, 12, 13, or 14, wherein step (a) comprises reacting the compound of formula VII with PIFA (preferably in a solvent which is THF), and preferably in anhydrous conditions, to form the compound of formula III, and reacting the compound of formula III with an acid.
16. A process according to Clause 14 or Clause 15, wherein the acid is hydrochloric acid, preferably concentrated hydrochloric acid.
17. A process according to any of Clauses 14, 15 or 16, wherein the reaction mixture is cooled prior to the addition of the acid, preferably wherein the reaction mixture is cooled to about −10° C. to about 10° C., about −5° C. to about 8° C., or about 0° C. to about 5° C.
18. A process according to any of Clauses 14, 15, 16, or 17, wherein the acid is added portionwise, or dropwise.
19. A process according to any of Clauses 14, 15, 16, 17, or 18, wherein the reaction mixture is maintained at a temperature of: about −10° C. to about 10° C., about −5° C. to about 8° C., or about 0° C. to about 5° C., preferably about −0° C. to about 5° C., during the addition of the acid.
20. A process according to any of Clauses 14, 15, 16, 17, 18, or 19, wherein after the addition of acid, the mixture is stirred, preferably at a temperature of: about 0° C. to about 20° C., about 5° C. to about 15° C., about 10° C. to about 12° C., or about 10° C.
21. A process according to Clause 20, wherein the mixture is stirred for a period of: about 4 hours to about 48 hours, about 6 hours to about 36 hours, about 6 hours to about 24 hours, about 6 hours to about 12 hours, or about 6 hours to about 8 hours.
22. A process according to any of Clauses 14, 15, 16, 17, 18, 19, 20, or 21, wherein the compound of formula IV is isolated by a process comprising the addition of one or more solvents, and a base (preferably wherein the base is an organic base, particularly selected from the group consisting of pyridine, pyrrolidine, N-methylpyridine, N-methylpiperidine, morpholine, and N-methylmorpholine (NMM)).
23. A process according to Clause 22, wherein the one or more solvents is selected from the group consisting of: water and/or an organic solvent selected from diethyl ether, diisopropyl ether, ethylacetate, and methylisobutyl ketone; preferably a mixture of water and an organic solvent selected from: diethyl ether, diisopropyl ether, ethylacetate, and methylisobutyl ketone; and more preferably a mixture of water and ethylacetate.
24. A process according to Clause 23, wherein the compound of formula IV is isolated by extraction into the organic solvent.
25. A process according to Clause 24, further comprising precipitation of the compound of formula IV by evaporation, and/or by the addition of antisolvent, preferably wherein the anti-solvent is selected from a $C_6$-$C_{10}$ alkane, preferably n-heptane.

26. A process according to any of Clauses 1-25, wherein the compound of formula VII is prepared by a process comprising:
(i) reacting the carboxylic acid group in the compound of formula OMV-1:

OMV-1

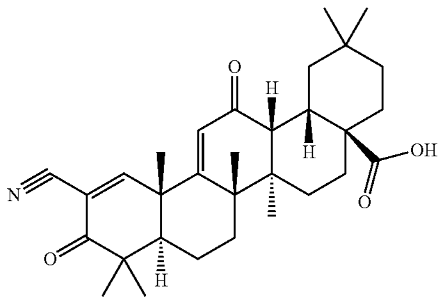

to form a compound of formula OMV-12A:

OMV-12A

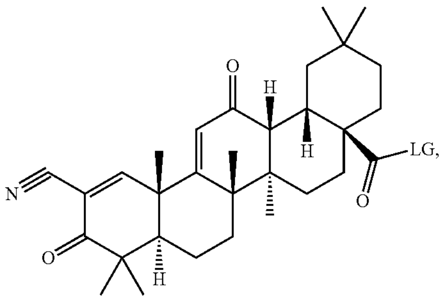

wherein LG is a leaving group, preferably fluoro, chloro or bromo, and more preferably chloro; and
(ii) aminolysis of the compound of formula OMV-12A to form the compound VII:

VII

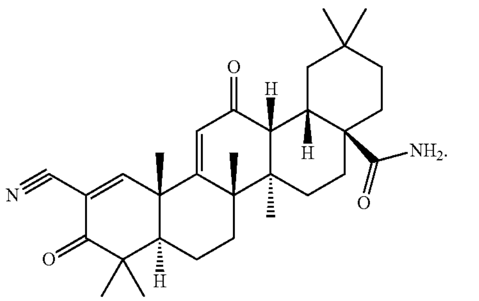

27. A process according to Clause 26, wherein the group LG in formula OMV-12A is chloro.
28. A process according to Clause 26 or Clause 27, wherein step (i) comprises reacting the compound of formula OMV-1 with a reagent selected from the group consisting of: thionyl chloride or phosphorus oxychloride, oxalyl chloride, preferably thionyl chloride; and/or step (i) is carried out in the presence of one or more solvents, preferably one or more aprotic solvents.
29. A process according to Clause 28, wherein the solvent comprises a hydrocarbon (particularly a $C_5$ to $C_{10}$ hydrocarbon, and more particularly toluene), and/or a polar aprotic solvent, preferably tetrahydrofuran (THF), dimethylsulfoxide (DMSO) or N,N-dimethylformamide (DMF), more preferably DMF.
30. A process according to Clause 28 or Clause 29, wherein step (i) is carried out in a solvent comprising toluene and DMF.
31. A process according to any of Clauses 26, 27, 28, 29, or 30, wherein the compound of formula OMV-12A is isolated, preferably wherein the compound is isolated by precipitation from the reaction mixture.
32. A process according to Clause 31, wherein the compound of formula OMV-12A is precipitated from the reaction mixture by addition of an antisolvent, preferably wherein the antisolvent is an alkane, more preferably a $C_5$ to $C_8$ alkane, and most preferably n-heptane.
33. A process according to Clause 31 or Clause 32, wherein the compound of formula OMV-12A is precipitated as crystals.
34. A process according to any of Clauses 26, 27, 28, 29, 30, 31, 32, or 33, wherein step (ii) is carried out in a suitable solvent, preferably a polar aprotic solvent, more preferably tetrahydrofuran.
35. A process according to any of Clauses 26, 27, 28, 29, 30, 31, 32, 33, or 34, wherein step (ii) is carried out by combining the compound of formula OMV-12A, preferably as a solution in the solvent, with ammonia or ammonium hydroxide.
36. A process according to Clause 35, wherein the ammonia or ammonium hydroxide is provided as a solution in a solvent, preferably the same solvent as for compound OMV-12A.
37. A process according to any of Clauses 34, 35 or 36, wherein step (ii) comprises addition of a solution of the compound of formula OMV-12A to a solution of ammonia or ammonium hydroxide.
38. A process according to Clause 37, wherein the addition of the solution of the compound of formula OMV-12A is carried out dropwise.
39. A process according to any of Clauses 26, 27, 28, 29, 30, 31, 32, 33, 34, 35, 36, 37, or 38, wherein the product compound VII from step (ii) of this process is isolated by filtration of the reaction mixture.
40. A process according to any of Clauses 1-39, wherein the compound of formula (VII) is prepared by a process comprising:
(i) reacting the compound of formula OMV-1:

OMV-1

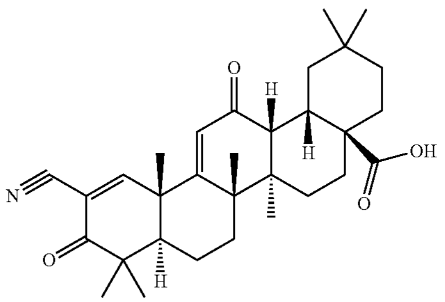

with 1,1'-carbonyldiimidazole (CDI) to form a compound of formula OMV-13:

OMV-13

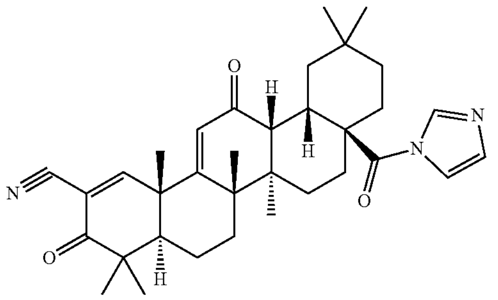

(ii) reacting the compound of formula OMV-13 with ammonia or ammonium hydroxide to form the compound VII:

VII

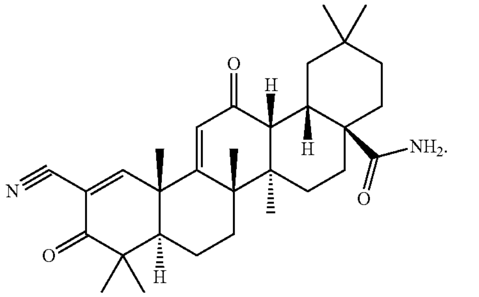

41. A process according to Clause 40, wherein step (i) is carried out in the presence of one or more solvents, preferably one or more aprotic solvents.
42. A process according to Clause 41, wherein the solvent comprises a polar aprotic solvent, preferably THF, DMSO or DMF, and more preferably the solvent comprises THF.
43. A process according to any of Clauses 40, 41 or 42, wherein step (ii) is carried out without isolating the compound of formula OMV-13.
44. A process according to any of Clauses 40, 41, 42, or 43, wherein compound OMV-13 is reacted with ammonia or ammonium hydroxide in situ, i.e. steps (i) and (ii) may be carried out in one pot.
45. A process according to any of Clauses 40, 41, 42, 43, or 44, wherein step (ii) comprises reaction of OMV-13 with ammonia.
46. A process according to Clause 45, wherein the reaction of OMV-13 with ammonia is carried out in a solvent comprising a polar aprotic solvent, preferably THF, DMSO or DMF, and more preferably THF.
47. A process according to Clause 45 or Clause 46 wherein step (ii) comprises addition of ammonia gas to a solution of compound OMV-13 in THF, preferably wherein the solution of OMV-13 in THF is obtained directly as the reaction mixture from step (i).
48. A process according to any of Clauses 45, 46 or 47, wherein step (ii) comprises reaction of OMV-13 with ammonia gas under pressure.
49. A process according to any of Clauses 40, 41, 42, 43, 44, 45, 46, 47, or 48, wherein step (ii) further comprises removal of the reaction solvent, for example by evaporation.
50. A process according to any of Clauses 40, 41, 42, 43, 44, 45, 46, 47, 48, or 49, wherein after the reaction, an acid, preferably acetic acid, and optionally a polar aprotic solvent, particularly THF, DMF or acetonitrile, more preferably acetonitrile, is added.
51. A process according to any of Clauses 40, 41, 42, 43, 44, 45, 46, 47, 48, 49, or 50, wherein the compound of formula (VII) is isolated from the mixture by crystallisation, preferably wherein the crystallisation comprises addition of an antisolvent.
52. A process according to Clause 51, wherein the antisolvent is water.
53. A process according to Clause 51 or Clause 52, wherein the compound of formula (VII) is obtained as a crystalline material.
54. A process according to any of Clauses 1-53, wherein step (b) comprises reacting the compound of formula IV with 2,2-difluoropropanoic acid to form Omaveloxolone.
55. A process according to Clause 54, wherein step (b) is carried out in the presence of a coupling agent and optionally a base.
56. A process according to Clause 55, wherein the coupling agent is dicyclohexylcarbodiimide (DCC) or 2-chloro-4,6-dimethoxy-1,3,5-triazine (CDMT), preferably CDMT.
57. A process according to any of Clauses 54, 55 or 56, wherein step (b) is carried out in the presence of a base, preferably wherein the base is selected from an organic base, and more particularly 4-(dimethylamino)pyridine (DMAP) or N-methylmorpholine (NMM), more particularly NMM.
58. A process according to any of Clauses 54, 55, 56, or 57, wherein the compound of formula IV is converted to Omaveloxolone by reaction with 2,3-difluoropropanoic acid in the presence of CDMT and NMM.
59. A process according to any of Clauses 54, 55, 56, 57, or 58, wherein step (b) is conducted in a solvent, wherein the solvent is preferably the solvent is an aprotic solvent, particularly selected from the group consisting of tetrahydrofuran (THF), 2-methyltetrahydrofuran (2-MeTHF), acetonitrile (ACN), ethylacetate, DMF or DMSO, more particularly THF or 2-MeTHF, and most particularly 2-Me-THF.
60. A process according to any of Clauses 54, 55, 56, 57, 58, or 59, wherein step (b) comprises combining the compound of formula IV with the coupling agent, base, and solvent; preferably wherein step (b) comprises combining the compound of formula IV with a mixture comprising CDMT and NMM in the solvent (preferably 2-MeTHF) and adding the compound IV to the mixture.
61. A process according to any of Clauses 54, 55, 56, 57, 58, 59, or 60, wherein the compound of formula IV is added as a solution, preferably in the same reaction solvent, preferably wherein the addition of compound IV is carried out at a temperature of from: about −10° C. to about 15° C., about −5° C. to about 10° C., or about 0 to about 5° C.
62. Omaveloxolone obtainable by a process according to any preceding claim.
63. Omaveloxolone according to Clause 62 which is chemically pure, preferably which has a purity of:

greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100%.

64. Omaveloxolone according to Clause 62 or Clause 63, which is enantiomerically pure, preferably containing: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide.

65. A compound of formula IV-A:

IV-A

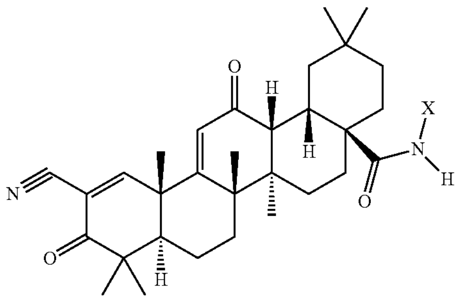

wherein X is selected from the group consisting of: chloro, bromo, iodo, or $Pb(OAc)_3$; or wherein X is selected from the group consisting of:

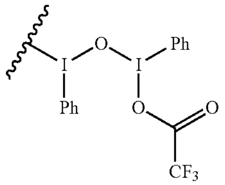

or

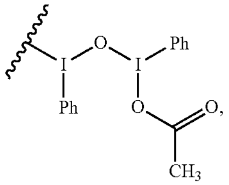

and preferably wherein X is:

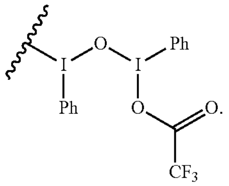

66. A compound according to Clause 65, which is chemically pure, preferably having a purity of greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100%.

67. A compound according to Clause 65 or Clause 66, which is enantiomerically pure, preferably containing: greater than 80% (w/w), greater than 90% (w/w), greater than about 95% (w/w), greater about 98% (w/w), greater than about 99% (w/w), greater than about 99.5% (w/w), greater than about 99.8% (w/w), greater than about 99.9% (w/w), greater than about 99.95% (w/w), or about 100% of the compound of formula:

IV-A

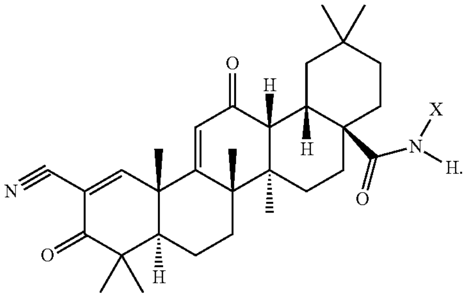

68. Use of a compound of formula VII or IV-A:

VII

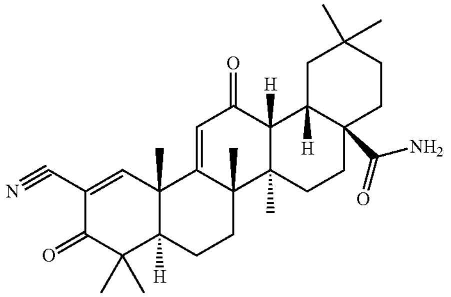

IV-A

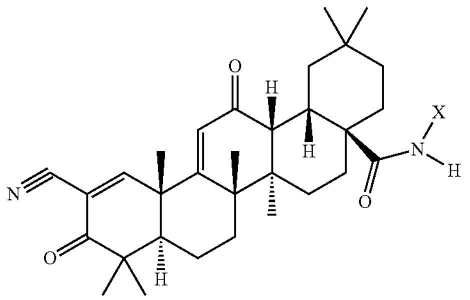

wherein the compound of formula IV-A is as defined in any of Clauses 65, 66 or 67, for the preparation of a compound of formula IV, or for the preparation of Omaveloxolone or a salt thereof.

69. A process for the preparation of a compound of formula (IV):

IV

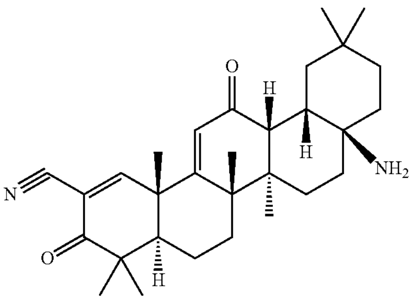

comprising Hofmann rearrangement of a compound of Formula VII:

VII

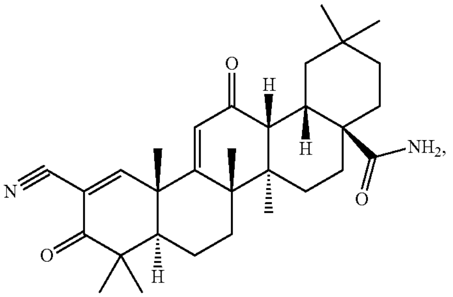

preferably wherein the Hofmann rearrangement is carried out by reaction of the compound of formula VII with a reagent selected from the group consisting of:

bromine or chlorine in the presence of an alkali metal hydroxide, preferably wherein the alkali metal hydroxide is sodium hydroxide;

sodium hypochlorite;

sodium hypobromite;

lead tetraacetate in the presence of a trialkylamine, preferably a tri($C_1$-$C_4$)alkylamine, and more preferably triethylamine;

N-bromosuccinimide in the presence of 1,8-diazabicyclo[5.4.0]undec-7-ene;

(bis(trifluoroacetoxy)iodo)benzene (PIFA); or (diacetoxyiodo)benzene (PIDA); and preferably wherein the reagent is (bis(trifluoroacetoxy)iodo)benzene (PIFA); or (diacetoxyiodo)benzene (PIDA), and more preferably wherein the reagent is (bis(trifluoroacetoxy)iodo)benzene (PIFA), followed by addition of a mineral acid, preferably hydrochloric acid.

70. A process according to Clause 69, wherein the Hofmann rearrangement is carried out according to the process of any of Clauses 2 to 25.

The invention claimed is:

1. A process for preparation of Omaveloxolone or a salt thereof, comprising:

(a) Hofmann rearrangement reaction of a compound of Formula VII with PIFA or PIDA, in a solvent selected from ethers, ketones, nitriles, and combinations thereof, wherein the reaction is carried out in anhydrous conditions:

VII

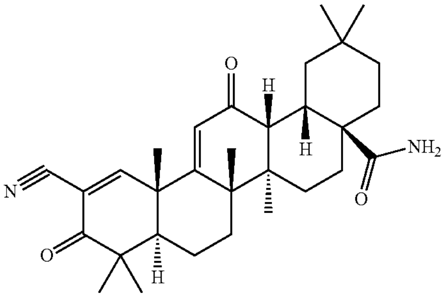

to form a compound of formula IV:

IV

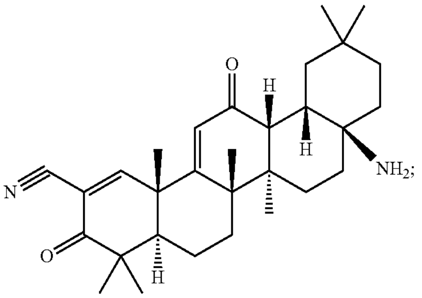

and (b) converting the compound of formula IV to Omaveloxolone.

2. A process for preparation of Omaveloxolone or a salt thereof, comprising:

(a) Hofmann rearrangement reaction of a compound of Formula VII with PIFA in anhydrous tetrahydrofuran:

VII

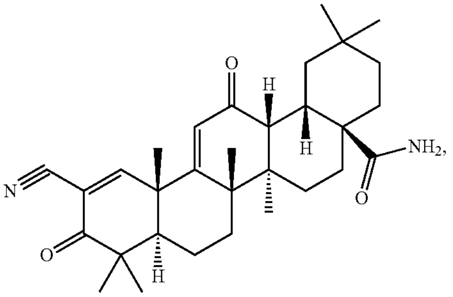

to form a compound of formula IV:

IV

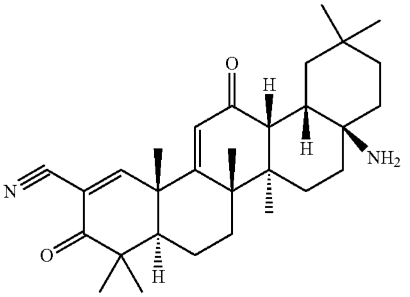

and (b) converting the compound of formula IV to Omaveloxolone.

3. A process according to claim 1, wherein step (a) further comprises adding a mineral acid selected from hydrochloric acid, sulfuric acid, nitric acid, or phosphoric acid.

4. A process according to claim 1, wherein the compound of formula VII is prepared by a process comprising:

(i) reacting the carboxylic acid group in the compound of formula OMV-1:

OMV-1

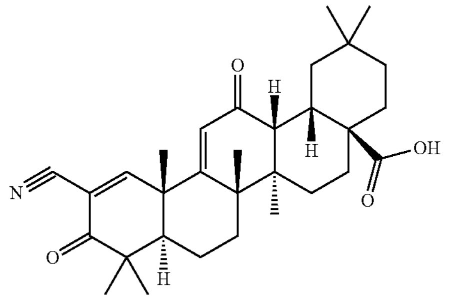

to form a compound of formula OMV-12A:

OMV-12A

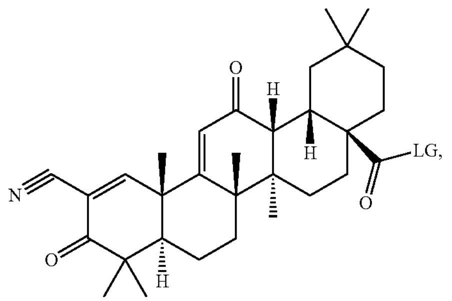

wherein LG is a leaving group selected from fluoro, chloro or bromo; and (ii) aminolysis of the compound of formula OMV-12A to form the compound of formula VII:

VII

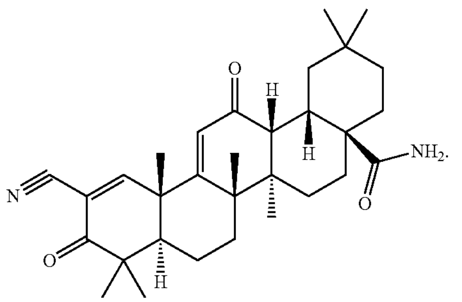

5. A process according to claim 1, wherein, the compound of formula (VII) is prepared by a process comprising:

(i) reacting the compound of formula OMV-1:

OMV-1

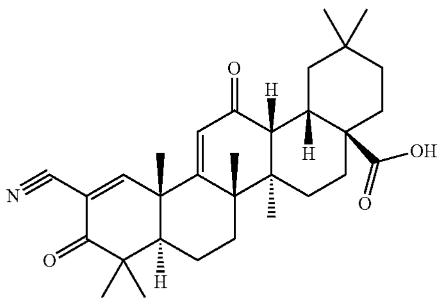

with 1,1'-carbonyldiimidazole (CDI) to form a compound of formula OMV-13:

OMV-13

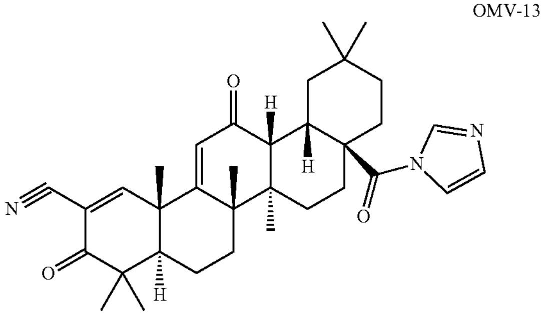

(ii) reacting the compound of formula OMV-13 with ammonia or ammonium hydroxide to form the compound VII:

VII

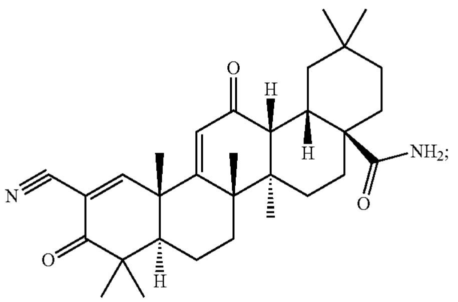

wherein step (ii) is carried out without isolating the compound of formula OMV-13.

6. A process according to claim 2, wherein step (a) further comprises adding a mineral acid selected from hydrochloric acid, sulfuric acid, nitric acid, or phosphoric acid.

7. A process according to claim 2, wherein the compound of formula VII is prepared by a process comprising:

(i) reacting the carboxylic acid group in the compound of formula OMV-1:

OMV-1

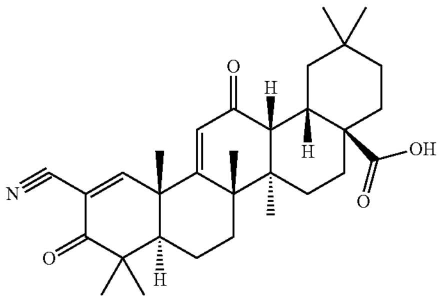

to form a compound of formula OMV-12A:

OMV-12A

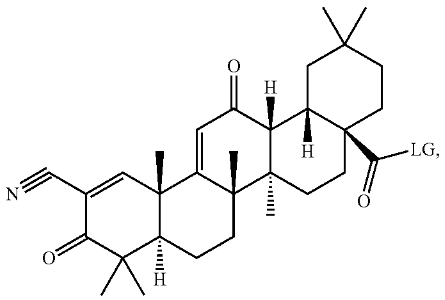

wherein LG is a leaving group selected from fluoro, chloro or bromo; and (ii) aminolysis of the compound of formula OMV-12A to form the compound of formula VII:

VII

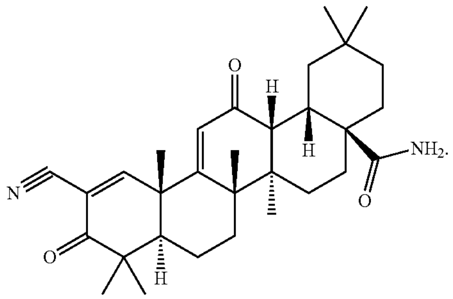

8. A process according to claim 2, wherein, the compound of formula (VII) is prepared by a process comprising:

(i) reacting the compound of formula OMV-1:

OMV-1

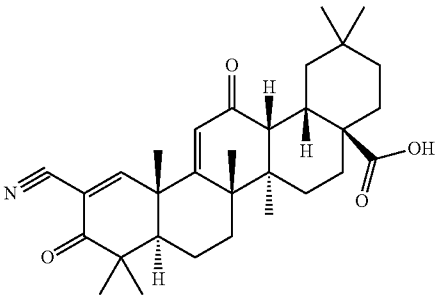

with 1,1'-carbonyldiimidazole (CDI) to form a compound of formula OMV-13:

OMV-13

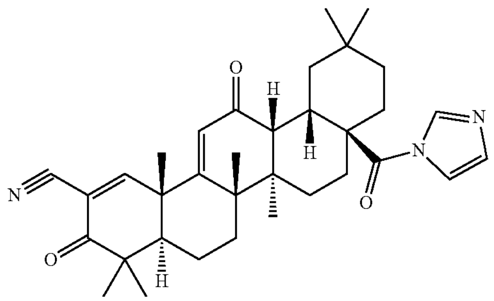

(ii) reacting the compound of formula OMV-13 with ammonia or ammonium hydroxide to form the compound VII:

VII

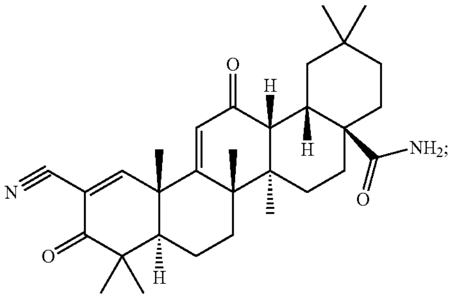

wherein step (ii) is carried out without isolating the compound of formula OMV-13.

* * * * *